United States Patent [19]

Minato

[11] Patent Number: 5,249,034
[45] Date of Patent: Sep. 28, 1993

[54] METHOD OF AND APPARATUS FOR INSPECTING END OF OBJECT FOR DEFECT

[75] Inventor: Nobuhiro Minato, Tokyo, Japan

[73] Assignee: Toyo Glass Co., Ltd., Tokyo, Japan

[21] Appl. No.: 820,975

[22] Filed: Jan. 15, 1992

[30] Foreign Application Priority Data

Jan. 29, 1991 [JP] Japan ................................. 3-026729

[51] Int. Cl.⁵ ...................... G01B 11/14; G01N 21/00
[52] U.S. Cl. .................................. 356/375; 356/237; 356/240; 356/394; 250/223 B; 358/101; 358/106; 209/526
[58] Field of Search ............... 356/375, 376, 240, 237, 356/239, 394, 426–428; 250/561, 562, 223 B, 563; 358/106, 101, 107; 382/8; 209/526, 522, 524, 528; 364/507, 552

[56] References Cited

U.S. PATENT DOCUMENTS

| | | |
|---|---|---|
| 4,300,689 | 11/1981 | Franklin et al. ................ 250/223 B |
| 4,343,553 | 8/1982 | Nakagawa et al. ................ 356/376 |
| 4,376,951 | 3/1983 | Miyazawa ........................ 250/223 B |
| 4,492,476 | 1/1985 | Miyazawa ............................ 358/106 |
| 4,606,635 | 8/1986 | Miyazawa et al. ............... 356/240 |
| 4,650,326 | 3/1987 | Nagamine et al. ............. 250/223 B |
| 4,736,851 | 4/1988 | Rieros et al. ........................ 209/526 |

FOREIGN PATENT DOCUMENTS 1-129112 5/1989 Japan .
2096763 2/1982 United Kingdom ............ 250/223 B Primary Examiner—Richard A. Rosenberger
Assistant Examiner—Hoa Q. Pham
Attorney, Agent, or Firm—Sughrue, Mion, Zinn, Macpeak & Seas

[57] ABSTRACT

A method of and an apparatus for inspecting an end of an object for a defect by which not only a defect caused by deformation of an end of an object in a horizontal direction but also another defect caused by deformation in a vertical direction can be detected with a high degree of accuracy. Light from an end portion of an object is received by a pair of one- or two-dimensional image sensors and disposed at a predetermined angle relative to each other, and brightness outputs of individual picture elements of the image sensors are stored into memories. From the stored signals, a bright line produced by light from an edge of the object end portion is detected for each image sensor, and a position of the bright line is calculated as a digital amount from a number of picture elements for each image sensor. Then, the digital amounts are added and substracted between the image sensors. A defect is judged from results of the addition and subtraction.

16 Claims, 5 Drawing Sheets

METHOD OF AND APPARATUS FOR INSPECTING END OF OBJECT FOR DEFECT

BACKGROUND OF THE INVENTION

1. Field of the Invention

This invention relates to a method of and an apparatus for inspecting an end portion of an object for a defect.

2. Description of the Prior Art

A method of inspecting a lip of a glass for a defect is conventionally known and disclosed, for example, in JP-A-1-129112. According to the method disclosed, light is projected to the opposite inner and outer portions of a lip of an object, and reflected light from the inner and outer portions of the lip is received by a single one-dimensional image sensor. When an output of the image sensor is taken out, if the lip is normal, then the output presents two pulses corresponding to reflected light from the inner and outer portions of the lip. The distance between the two pulses varies in accordance with a thickness of the lip while the widths of the pulses vary in accordance with a height of the lip but by small amounts. Thus, according to the method, the distance between the two pulses is compared with a reference value to detect an abnormal thickness of the lip, and the widths of the pulses are compared with a reference value to detect an abnormal height of the lip. Besides, the fact that the lip has some uneven or convex and concave profile is detected from absence of either of such pulses.

According to the conventional method, a satisfactory result of inspection is obtained for a defect caused by deformation of the lip in a horizontal direction since a pulse varies in response to a variation of the lip in the horizontal direction by an amount which increases in proportion to such variation of the lip. However, since the width of a pulse varies in response to a variation of the lip in a vertical direction but by a small amount, a satisfactory result of inspection cannot be obtained for a defect caused by deformation of the lip in the vertical direction. Although it is possible to detect, using the conventional method, a significantly uneven, convex and concave profile of a lip because a pulse is absent, it is very difficult to detect a defect such as a down sealing surface or a waving surface of a lip of an object which presents a continuously and moderately deformed profile in a vertical direction.

SUMMARY OF THE INVENTION

It is an object of the present invention to provide a method of and an apparatus for inspecting an end of an object for a defect by which not only a defect caused by deformation of an end of an object in a horizontal direction but also another defect caused by deformation in a vertical direction can be detected with a high degree of accuracy.

In order to attain the object, according to the present invention, there is provided a method of inspecting an end portion of an object for a defect, which comprises the steps of receiving light from an end portion of an object by means of a pair of one- or two-dimensional image sensors disposed at a predetermined angle relative to each other, storing brightness outputs of individual picture elements of the image sensors into a memory, detecting, from the brightness signals from the memory, a bright line provided by light from an edge of the end portion of the object individually for the image sensors, calculating positions of the bright lines as digital amounts from numbers of picture elements individually for the image sensors, adding and subtracting the digital amounts to and from each other between the image sensors, and judging a defect from any of results of such addition and subtraction.

With the inspecting method, light from an end portion of an object is received by the pair of one- or two-dimensional image sensors, and brightness outputs of the picture elements of the image sensors are stored into the memory. A bright line provided by light from an edge of the end portion of the object is detected for each of the image sensors from the brightness signals from the memory, and positions of the bright lines are calculated as digital amounts from numbers of picture elements individually for the image sensors. The digital amounts thus obtained are added to and subtracted from each other between the image sensors. By such addition and subtraction, a variation of the edge of the end portion of the object can be extracted as a horizontal component and a vertical component, and a defect is judged from results of such addition and subtraction. Accordingly, not only a defect caused by deformation of the end portion of the object in the horizontal direction but also another defect caused by deformation of the end portion of the object in the vertical direction can be detected with a high degree of accuracy.

In accordance with the present invention, the inspecting method is carried out by an apparatus for inspecting an end portion of an object for a defect, which comprises means for rotating or moving an object for inspection, a light source for projecting light upon an end portion of the object, a pair of one- or two-dimensional image sensors disposed at a predetermined angle relative to each other for receiving reflected light from the end portion of the object at different angles, an A/D converter for converting an analog output of each of the image sensors into a digital value, a memory for storing the digital data obtained by such conversion for individual picture elements therein, bright line detecting means for detecting, from the stored data, picture elements having brightness values higher than a predetermined threshold value for each of the image sensors to detect a bright line provided by light from the edge of the end portion of the object for each of the image sensors, bright line position detecting means for calculating a position of the bright line as a digital amount from a number of picture elements for each of the image sensors, adding means and subtracting means for adding and subtracting the digital amounts to and from each other, and defect judging means for judging a defect from any of results of such addition and subtraction.

With the inspecting apparatus, not only a defect of the end portion of the object caused by deformation in a horizontal direction but also another defect caused by deformation in a vertical direction can be detected with a high degree of accuracy.

Preferably, the inspecting apparatus further comprises average value calculating means for calculating an average value between those of the results of the subtraction obtained by said subtracting means for two points which are spaced from each other in a direction of the length of the bright line. Thus, also an eccentricity of an end portion of an object can be detected.

The above and other objects, features and advantages of the present invention will become apparent from the following description and the appended claims, taken in conjunction with the accompanying drawings.

DESCRIPTION OF THE PREFERRED EMBODIMENTS

Figure 1:
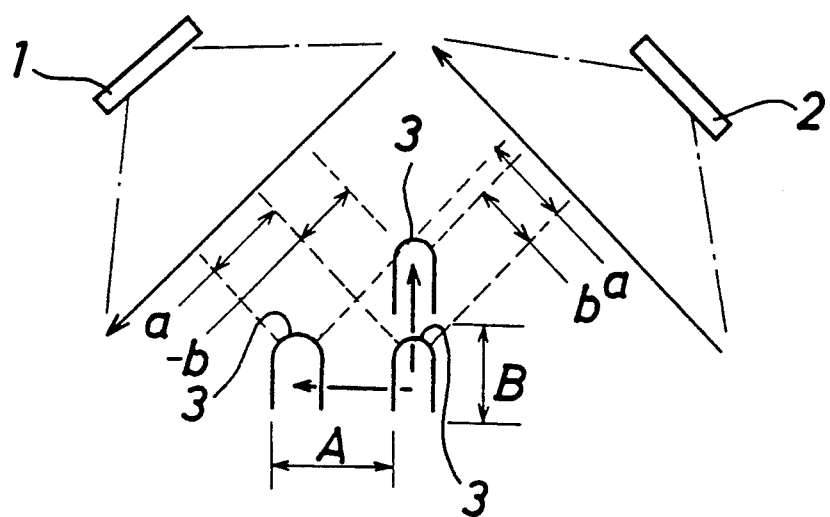
FIG. 1 is a diagrammatic representation illustrating a concept of an inspecting method according to the present invention.

Referring first to FIG. 1, there is illustrated a conceptual diagram of an inspecting method according to the present invention. The inspecting method is carried out with an inspecting apparatus wherein first and second image sensors 1 and 2 are disposed at obliquely upper positions on the opposite sides of an upper end portion 3 of an object for inspection such that reflected light from the object end portion 3 is received by the image sensors 1 and 2. Here, it is assumed that the object end portion 3 is displaced by a variation A in a horizontal direction and by another variation B in a vertical direction, and the first and second image sensors 1 and 2 are inclined by 90 degrees relative to each other and by 45 degrees with respect to the horizontal and vertical directions of such movement of the object end portion 3 as illustratively shown in FIG. 1. A total variation of the object end portion 3 detected by the first image sensor 1 is represented by S1 while a total variation of the object end portion 3 detected by the second image sensor 2 is represented by S2. The total variations S1 and S2 can be individually calculated from numbers of picture elements as counted with the image sensors 1 and 2. Either of the total variations S1 and S2 is a composite of a variation in the horizontal direction and another variation in the vertical direction. When the variations are calculated by counting numbers of picture elements from above to below with the first image sensor 1 and from below to above with the second image sensor 2 as indicated by arrow marks individually assigned to the image sensors 1 and 2, variations a in the horizontal direction are equal in absolute value and same in sign between the two image sensors 1 and 2, but the variations b in the vertical direction are equal in absolute value but opposite in sign to each other. In particular, if the object end portion 3 moves in the leftward direction in FIG. 1 by the distance A, then it moves, on each of the image sensors 1 and 2, by the variation a in the direction indicated by the arrow mark assigned thereto. But, if the object end portion 3 moves in the upward direction in FIG. 1 by the distance B, then it moves by the distance b on the first image sensor 1 but in the direction opposite to the direction of the arrow mark assigned thereto, but it moves by the same distance b on the second image sensor 2 in the direction of the arrow mark. Consequently, when the object end portion 3 makes a composite movement between such movements, it moves, on the first image sensor 1, by a distance equal to a+(−b), but it moves, on the second image sensor 2, by another distance equal to a+b. Accordingly, the variations S1 and S2 can be represented as S1=a−b and S2=a+b, respectively.

Thus, by adding the variations S1 and S2, $$S1+S2=(a-b)+(a+b)=2a$$

is obtained, and consequently, the variations in the vertical direction are deleted while only the variations in the horizontal direction remain. Meanwhile, by subtracting the variation S2 from the variation S1, $$S1-S2=(a-b)-(a+b)=-2b$$

is obtained, and consequently, the variations in the horizontal direction are deleted while only the variations in the vertical direction remain by taking an absolute value of the result of the subtraction.

In short, if digital amounts representing positions of bright lines obtained from the image sensors 1 and 2 are added to and subtracted from each other, then variations of edges of the object end portion 3 can be taken out as a horizontal component and a separate vertical component. Accordingly, not only a defect of an object end portion caused by deformation of the object end portion in a horizontal direction but also another defect caused by deformation in a vertical direction can be detected with a high degree of accuracy.

Figure 2:
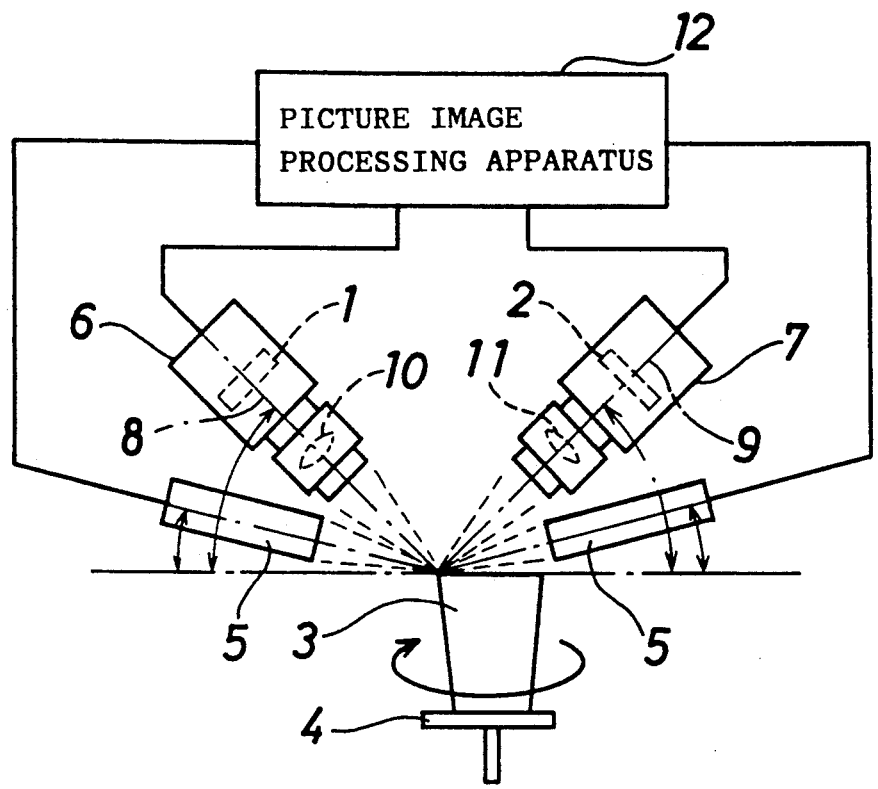
FIG. 2 is a schematic diagrammatic view illustrating a manner of carrying out an inspecting method according to the present invention.
Figure 3:
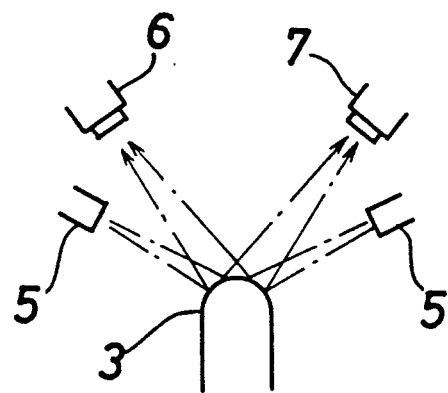
FIG. 3 is a diagrammatic representation showing routes of light in the inspecting method illustrated in FIG. 2.

The inspecting method will be described more in detail with reference to FIG. 2 wherein it is used to inspect a lip of a glass for a defect. Glasses 3 of objects for inspection are transported one after another to a horizontal turntable 4 by means of a conveyor not shown. A glass 3 on the turntable 4 is rotated at least by one full rotation by the turntable 4. A pair of light sources 5 are disposed above the level of the turntable 4 such that they project light obliquely to the opposite inner and outer portions of a lip of the glass 3, and a pair of CCD cameras 6 and 7 for photographing illuminated locations of the glass 3 are disposed in a corresponding relationship above the light sources 5. The CCD cameras 6 and 7 are inclined such that optical axes 8 and 9 thereof make an equal angle (for example, 45 degrees) on the opposite sides with respect to a top face of the lip of the glass 3, and the first CCD camera 6 photographs an illuminated portion of the lip of the glass 3 obliquely from the outside of the glass 3 while the second CCD camera 7 photographs another illuminated portion of the lip of the glass 3 obliquely from the inside of the glass 3. Routes of reflected light from the lip of the glass 3 in this instance are illustrated in FIG. 3. The CCD cameras 6 and 7 have lenses 10 and 11 and one-dimensional image sensors (line sensors) 1 and 2, respectively. Each of the one-dimensional image sensors 1 and 2 has a large number of photoelectric transducer elements disposed in a vertical column. Thus, reflected light from the lip of the glass 3 is condensed by the lenses 10 and 11 and introduced into the image sensors 1 and 2. Outputs of the image sensors 1 and 2 are converted into digital values by and fetched into a picture image processing apparatus 12 which includes a CPU (central processing unit), a RAM (random access memory), a ROM (read only memory) and so forth so that they are picture processed by the picture image processing apparatus 12 to inspect the lip of the glass 3 for a defect.

Figure 5:
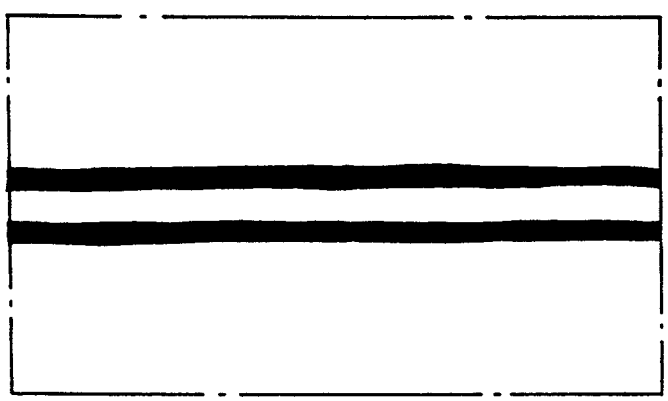
FIG. 5 is a diagram showing bright lines photographed by a CCD camera when a lip of a glass is normal.
Figure 6:
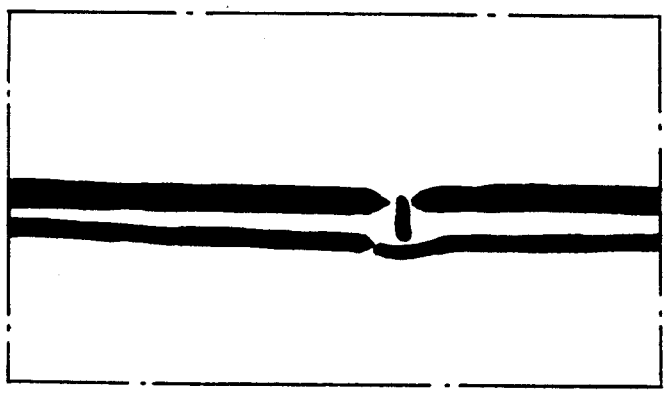
FIG. 6 is a similar view but showing bright lines when a lip of a glass photographed by the CCD camera has a stepped portion thereon.
Figure 7:
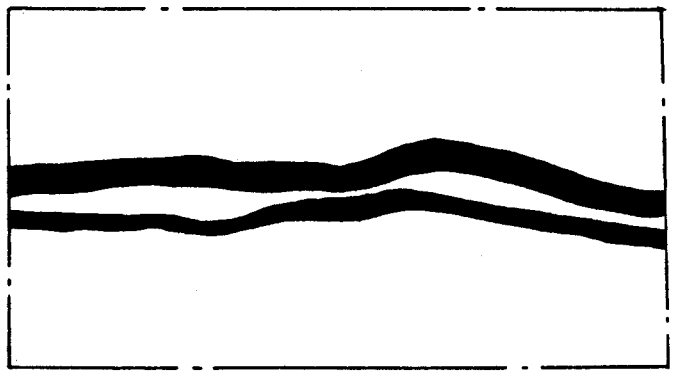
FIG. 7 is a similar view but showing bright lines when the top face of a lip of a glass photographed has a corrugated profile.

Of light reflected from the lip of the glass 3 and introduced into the CCD cameras 6 and 7, light from two edges of the lip is highest in amount. Since the glass 3 is being rotated, when the CCD cameras 6 and 7 successively photograph the lip of the glass 3 at a sufficiently small pitch, reflected light from the edges on the opposite inner and outer sides of the lip are photographed as two bright lines as shown in FIG. 5 by each of the CCD cameras 6 and 7. Such two bright lines make, when the lip is normal, substantially parallel straight lines with both of the two CCD cameras 6 and 7. However, in case the lip has, for example, a stepped portion (so-called step defect), part of the bright lines is omitted or a protruded portion appears on either one of the bright lines as shown in FIG. 6 with both of the two CCD cameras 6 and 7. On the other hand, when the top face of the lip has a corrugated profile (so-called waving surface defect), the two bright lines present corrugated shapes as shown in FIG. 7. According to the present invention, a defect of a lip is detected by detecting such an abnormal condition of a bright line as described above.

Figure 4:
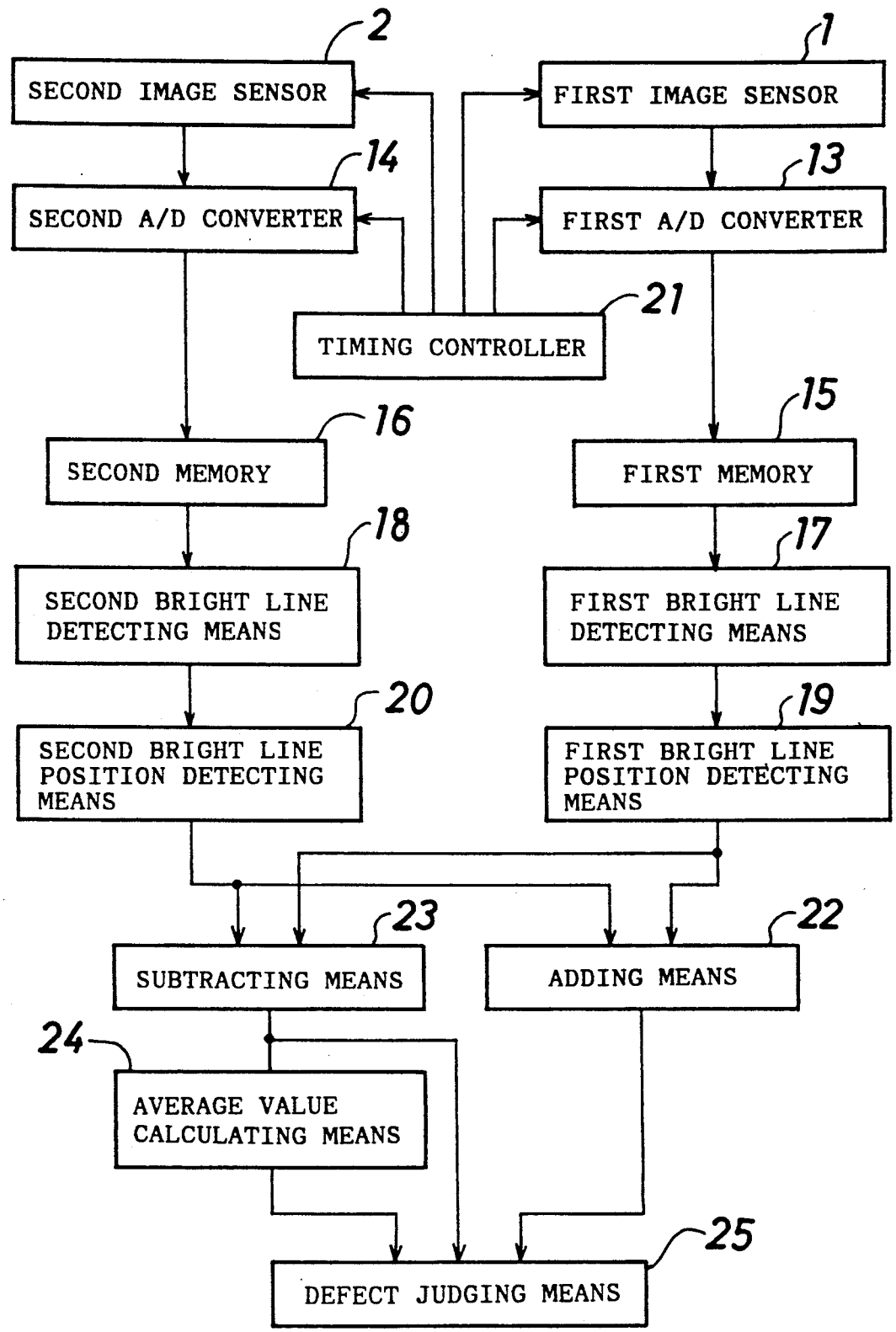
FIG. 4 is a block diagram of an inspecting apparatus according to the present invention.

General construction of the picture image processing apparatus 12 is shown in FIG. 4 wherein the picture image processing apparatus 12 is shown constructed from different functions controlled by the CPU. Referring to FIG. 4, the picture image processing apparatus 12 shown includes first and second analog to digital (A/D) converters 13 and 14, first and second memories 15 and 16, first and second bright line detecting means 17 and 18 and first and second bright line position detecting means 19 and 20 all connected in series to the first and second image sensors 1 and 2, respectively. The picture image processing apparatus 12 further includes a timing controller 21, a subtracting means 23 and an adding means 23, an average value calculating means 24 and a defect judging means 25 connected commonly to the first and second series of circuits.

Analog outputs of the first and second image sensors 1 and 2 are fetched in response to a speed of rotation of the glass 3 under the control of the timing controller 21 and converted into digital values by the first and second A/D converters 13 and 14, respectively. Then, digital data from the first and second A/D converters 13 and 14 for one full rotation of the glass 3 are stored separately for individual picture elements into the memories 15 and 16, respectively. In short, a developed view of an entire circumference of the lip of the glass 3 as viewed from an obliquely upper position on the outer side of the glass 3 is divided into a large number of increments corresponding to individual picture elements, and brightness levels are stored into the first memory 15 for the individual increments. Also, another developed view of the lip as viewed from another obliquely upper position on the inner side is similarly divided into a large number of increments and brightness levels are stored into the second memory 16 for the individual increments.

The first bright line detecting means 17 detects, from among the picture element data for one rotation of the glass 3 stored in the first memory 15, those picture element data which are higher than a predetermined threshold value, in short, those picture elements which have brightness levels higher than a predetermined level, to detect two bright lines (sets of continuous picture elements having brightness values higher than the predetermined level) originating from the inner and outer edges of the lip of the glass 3. Similarly, the second bright line detecting means 18 detects, from among the picture element data for one rotation of the glass 3 stored in the second memory 16, those picture elements having brightness levels higher than the predetermined level to detect two bright lines. It is to be noted that a bright line can otherwise be detected from a peak in brightness.

Positions of those picture elements which are detected as constituting the bright lines by the first and second bright line detecting means 17 and 18 can each be determined by the number of elements included between the position and, when, for example, an upper end or a lower end of the vertical column of the elements of the image sensor 1 or 2 is fixed as a base point, the bright-line positions can be determined by the number of picture elements included between the position and the base point. Thus, the first bright line position detecting means 19 calculates positions of the two bright lines detected by the first bright line detecting means 17 from numbers of picture elements as counted in a downward direction from the upper base point while the second bright line position detecting means 20 calculates positions of the two bright lines detected by the second bright line detecting means 18 from numbers of picture elements as counted, in a reverse direction to that of counting by the first bright line position detecting means 19, in an upward direction from the lower base point (refer to the arrow marks assigned to the image sensors 1 and 2 in FIG. 1). In this instance, the position of each of the bright lines is calculated separately with regard to a large number of points thereof. Accordingly, the digital amounts obtained by the first bright line position detecting means 19 represent positions of a large number of points of the opposite inner and outer edges of the lip of the glass 3 as viewed from the obliquely upper outer position while the digital amounts obtained by the second bright line position detecting means 20 represent positions of a large number of points of the opposite inner and outer edges of the lip as viewed from the obliquely upper inner position.

The adding means 22 adds the digital amounts obtained by the second bright line position detecting means 20 to the digital amounts obtained by the first bright line position detecting means 19 while the subtracting means 23 subtracts the digital amounts obtained by the second bright line position detecting means 20 from the digital amounts obtained by the first bright line position detecting means 19. Results of such addition by the adding means 22 represent the positions of the edges in the horizontal direction while results of the subtraction by the subtracting means 23 represent the positions of the edges in the vertical direction as apparent from FIG. 1 and the foregoing description.

The average value calculating means 24 calculates, from the results of the subtraction by the subtracting means 23 derived from the position data of the large number of points in the vertical direction, an average value of position data of two points spaced by 180 degrees by rotational angle of the glass 3. Also such average value calculation is performed for a large number of points of each of the bright lines. If the lip of the glass 3 has an uneven or varying height, then the positions of the bright lines are displaced correspondingly. If the period of a change in position (a change in height) of each of the bright lines is equal to a period of rotation of the glass 3 and regular, then an average value of position data of two points spaced by an angular distance of 180 degrees from each other will be similarly constant as in the case of a glass which presents no change in height because variations of their positions cancel each other. On the contrary, if such positional change is irregular or the period of such change is different from the period of rotation of the glass 3, then the positional variations at the two points will not cancel each other, and consequently, an average value between them will not be constant. Further, the average value calculating means 24 also calculates a difference between position data of two points spaced by 180 degrees from each other.

It is to be noted that an average value of position data of two points spaced by 180 degrees by rotational angle of the glass 3 may be calculated similarly with regard to results of addition obtained by the adding means 22, in short, positional data of a large number of points in the horizontal direction. In this instance, if the lip of the glass 3 is deformed in an eccentric profile, then also the positions of the bright lines are displaced from positions of bright lines originating from the lip of the glass 3 when it has a profile of a correct circle. Accordingly, average values thus calculated represent amounts of eccentricity of the individual points of the lip.

The defect judging means 25 judges presence or absence of a defect and, if presence of a defect is detected, then, it judges a kind, a size and so forth of such defect, from a relationship in magnitude among the results of the addition obtained by the adding means 22, the results of the subtraction obtained by the subtracting means 23 and the average values obtained by the average value calculating means 24. For example, a down sealing surface which is a defect that the top face of a lip of a glass is inclined toward the inner side or the outer side and a degree of such defect can be detected by judgment in magnitude of the results of the subtraction. Further, a waving surface which is a defect that the top face of a lip of a glass presents a corrugated uneven profile and a degree of such defect can be detected by judgment in magnitude of the average values of the results of the subtraction. Furthermore, an eccentric condition of a lip of a glass and a degree of such eccentricity can be detected by judgment in magnitude of the results of the addition similarly as in the case of the results of the subtraction, and an elliptic mouth which is a defect of deformation of a mouth of a glass into an elliptic profile or a deformed mouth which is a defect of deformation of a mouth of a glass into an irregular profile and a degree of such defect can be detected by judgment in magnitude of average values of the results of the addition. Besides, a teardrop and a magnitude thereof can be detected by judgment in magnitude of the results of both of the addition and the subtraction. In addition, a defect that a bright line is broken such as a bad or faulty burn-off or a chipped finish can be detected by judgment in magnitude or length of such broken portion of the bright line. Also a defect such as fine glass or a bad fire finish can be detected by judgment in magnitude of the results of both of the addition and the subtraction. The defect judging means 25 outputs, when it judges that there is a defect, an excluding instruction signal to exclude the glass 3 from the transporting line.

Figure 8:
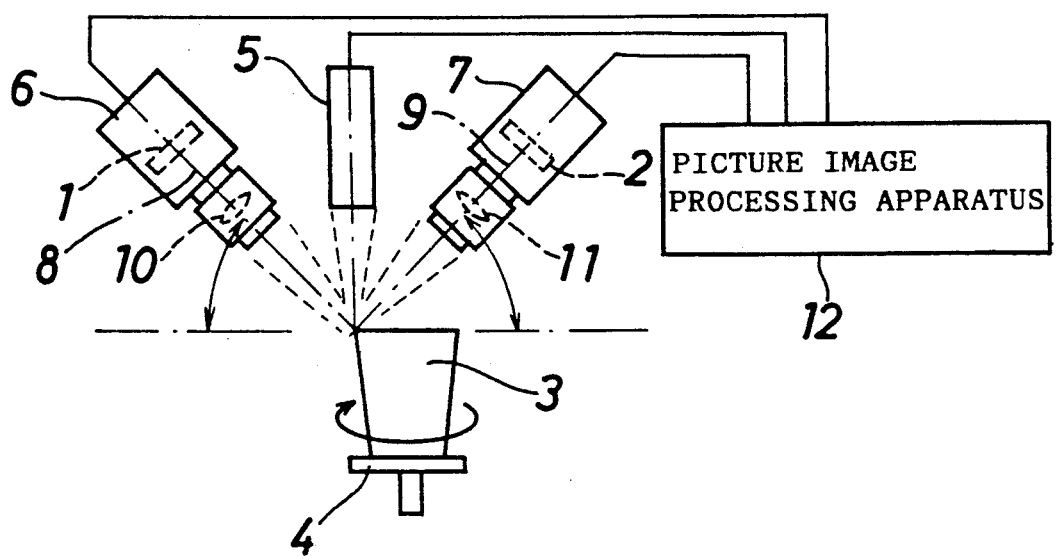
FIG. 8 is a schematic diagrammatic view illustrating another manner of carrying out the inspecting method of the present invention.
Figure 9:
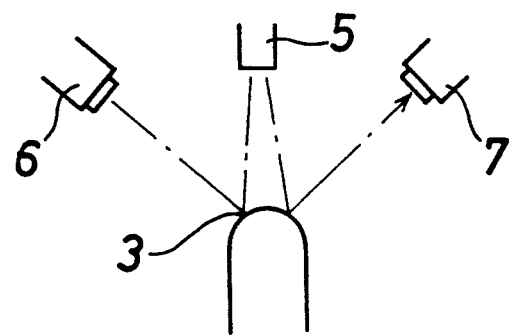
FIG. 9 is a diagrammatic representation showing routes of light in the inspecting method illustrated in FIG. 8.

While the light sources 5 are prepared individually for the two CCD cameras 6 and 7 in the embodiment described above, alternatively a single light source 5 may be installed intermediately between the CCD cameras 6 and 7 such that light may be projected from just above the lip of the glass 3 as shown in FIG. 8. Routes of reflected light in this instance are illustratively shown in FIG. 9. Further, while a one-dimensional image sensor is employed for each of the first and second image sensors 1 and 2, alternatively a two-dimensional image sensor (area sensor) may be employed. Furthermore, it is also possible to perform inspection using three or more image sensors. It is also possible to inspect an article of an object for inspection while the article is, for example, being moved linearly.

Having now fully described the invention, it will be apparent to one of ordinary skill in the art that many changes and modifications can be made thereto without departing from the spirit and scope of the invention as set forth herein.

What is claimed is:

1. A method of inspecting an end portion of an object for a defect, comprising the steps of receiving light from an end portion of an object by means of a pair of one- or two-dimensional image sensors disposed at a predetermined angle relative to each other, storing brightness outputs of picture elements of said image sensors into a memory, detecting, from the brightness signals from said memory, a bright line provided by light from an edge of the end portion of the object for each of said image sensors, calculating positions of the bright lines as digital amounts from numbers of picture elements individually for said image sensors, adding and subtracting the digital amounts to and from each other between said image sensors, and judging a defect from any of results of such addition and subtraction.

2. A method as claimed in claim 1, wherein picture elements having brightness values higher than a predetermined threshold value are detected for each of said image sensors to detect a bright line provided by light from an edge of an end portion of an object for each of said image sensors.

3. A method as claimed in claim 1, further comprising the step of calculating, subsequently to the adding and subtracting step, an average value between those of results of the addition or the subtraction for two points which are spaced from each other in a direction of the length of the bright line, and wherein, at the judging step, a defect is judged from any of the results of the addition and subtraction as well as the thus calculated average value.

4. An apparatus for inspecting an end portion of an object for a defect, comprising:
means for rotating or moving an object for inspection;
a light source for projecting light upon an end portion of the object;
a pair of one- or two-dimensional image sensors disposed at a predetermined angle relative to each other for receiving reflected light from the end portion of the object at different angles;
an A/D converter for converting an analog output of each of said image sensors into a digital value;

a memory for storing the digital data obtained by such conversion for individual picture elements therein;

bright line detecting means for detecting, from the stored data, picture elements having brightness values higher than a predetermined threshold value for each of said image sensors to detect a bright line provided by light from the edge of the end portion of the object for each of said image sensors;

bright line position detecting means for calculating a position of the bright line as a digital amount from a number of picture elements for each of said image sensors;

adding means and subtracting means for adding and subtracting the digital amounts to and from each other; and defect judging means for judging a defect from a result of such addition and a result of such subtraction.

5. An apparatus as claimed in claim 4, further comprising average value calculating means for calculating an average value between those of the results of the addition obtained by said adding means for two points which are spaced from each other in a direction of the length of the bright line.

6. An apparatus as claimed in claim 4, wherein said image sensors are disposed substantially at an angle of 90 degrees relative to each other and at an angle of 45 degrees with respect to a plane in which the object is rotated or moved.

7. An apparatus as claimed in claim 4, further comprising another light source for projecting light upon an end portion of an object, the two light sources being disposed corresponding to said image sensors.

8. A method of inspecting an end portion of an object for a defeat, comprising the steps of:

receiving light from the end portion by means of a plurality of image sensors disposed at predetermined angles relative to one another;

processing brightness outputs from the image sensors to provide brightness signals;

detecting, from the brightness signals, signals indicative of bright lines reflected from the end portion;

calculating positions of the bright lines and outputting digital values, representative of displacement variations of the end portion, for each image sensor;

summing those of the digital values that represent variations in a first coordinate direction;

calculating differences between those of the digital values that represent variations in a second coordinate direction; and processing results from said summing step and said difference calculating step to determine a defect in the end portion.

9. An apparatus for inspecting an end portion of an object for a defect, comprising:

a light source for projecting light upon the end portion;

a plurality of image sensors disposed at predetermined angles relative to one another for receiving light reflected from the end portion and providing a plurality of image signal outputs;

processing circuitry for providing a plurality of brightness outputs;

at least one bright-line detector for processing the brightness outputs to detect bright lines formed by light reflected from the end portion;

at least one bright-line position detector for outputting digital values for each image sensor representative of the position of the detected bright lines;

circuitry that adds predetermined ones of the digital values to form a signal indicative of displacement of the edge portion in a first coordinate direction;

circuitry that calculates differences between predetermined ones of the digital values to form a signal indicative of displacement of the edge portion in a second coordinate direction; and circuitry that receives and processes the output from said adding circuitry and the output from said difference calculating circuitry to determine defects in the end portion.

10. An apparatus as claimed in claim 9, wherein said plurality of image sensors is a pair of image sensors.

11. An apparatus as claimed in claim 9, wherein said image sensors are one-dimensional image sensors.

12. An apparatus as claimed in claim 9, wherein said image sensors are two-dimensional image sensors.

13. An apparatus as claimed in claim 9, further comprising an average value calculator for calculating an average value of predetermined ones of the digital values representative of the position of the detected bright lines.

14. An apparatus as claimed in claim 9, further comprising a support for supporting the object and moving the object relative to the plurality of image sensors.

15. An apparatus as claimed in claim 9, wherein the said image sensors each comprise a number of picture elements that supply analog image signal outputs.

16. An apparatus as claimed in claim 15, further comprising at least one analog-to-digital converter for converting the analog image signal outputs into digital outputs.

* * * * *